United States Patent [19]

Izumisawa et al.

[11] Patent Number: 5,557,009
[45] Date of Patent: Sep. 17, 1996

[54] PROCESS FOR PREPARING AN AQUEOUS SLURRY OF TEREPHTHALIC ACID

[75] Inventors: Yoshiaki Izumisawa, Tokyo; Yoshiyuki Sumi; Takayuki Isogai, both of Kitakyushu, all of Japan

[73] Assignee: Mitsubishi Chemical Corporation, Tokyo, Japan

[21] Appl. No.: 550,935

[22] Filed: Oct. 31, 1995

[30] Foreign Application Priority Data

Nov. 15, 1994 [JP] Japan .................................... 6-280910
Dec. 19, 1994 [JP] Japan .................................... 6-315019

[51] Int. Cl.$^6$ ................................................ C07C 51/265
[52] U.S. Cl. ............................ 562/412; 562/414; 562/486
[58] Field of Search ................................ 562/412–414, 562/486

[56] References Cited

U.S. PATENT DOCUMENTS 4,081,464 3/1978 Marsh et al. .
5,008,450 4/1991 Yamamoto et al. .
5,200,557 4/1993 Gee et al. .

FOREIGN PATENT DOCUMENTS 0502628    9/1992  European Pat. Off. .
2067563    7/1981  United Kingdom .
WO93/24440 12/1993 WIPO .

*Primary Examiner*—Samuel Barts
*Attorney, Agent, or Firm*—Oblon, Spivak, McClelland, Maier & Neustadt, P.C.

[57] ABSTRACT

A process for preparing an aqueous slurry of terephthalic acid, which comprises oxidizing p-xylene with molecular oxygen in a liquid phase in an acetic acid solvent in the presence of a catalyst, to obtain an acetic acid slurry of terephthalic acid, separating terephthalic acid crystals from the acetic acid slurry, washing the terephthalic acid crystals containing acetic acid, with p-xylene or an acetic acid ester, and then mixing water thereto.

26 Claims, No Drawings

PROCESS FOR PREPARING AN AQUEOUS SLURRY OF TEREPHTHALIC ACID

The present invention relates to a process for preparing an aqueous slurry of terephthalic acid by substituting water for the dispersing medium of an acetic acid slurry of terephthalic acid produced by oxidizing p-xylene in a liquid phase in acetic acid.

Terephthalic acid is produced usually by a so-called SD method wherein p-xylene is reacted with molecular oxygen in the presence of a catalyst which contains e.g. cobalt, manganese and bromine. From an acetic acid slurry of terephthalic acid thereby obtained as a reaction mixture, crude terephthalic acid is separated by crystallization. This crude terephthalic acid usually contains 4-carboxybenzaldehyde (hereinafter referred to as "4CBA") as an impurity in an amount of from 100 to 10,000 ppm by weight. Therefore, it is common to subject such crude terephthalic acid to purification by hydrogenation.

For such reduction purification, it is common to sufficiently dry the crude terephthalic acid containing acetic acid, to remove and recover the acetic acid. Then, the dried crude terephthalic acid is dispersed in water to obtain a slurry, which is pressurized and heated for complete dissolution. Then, the solution is contacted with a platinum group metal catalyst usually in the presence of hydrogen under a high pressure and high temperature condition for purification by hydrogenation, followed by crystallization to obtain crystals of purified terephthalic acid. This method has a problem that the operation is cumbersome, in addition to a disadvantage such that the installation cost in the production cost is high since installations are required for the drying, storage and re-slurrying the crude terephthalic acid.

Some proposals have been made for an improved method for substituting water for the dispersing medium of an acetic acid slurry of terephthalic acid. For example, U.S. Pat. No. 5,008,450 proposes a method wherein an acetic acid slurry of terephthalic acid is introduced from an upper portion of a multistage tower, while water is introduced from a lower portion of the tower, so that a rising current is formed in the multistage tower, while terephthalic acid particles are permitted to sediment, whereby acetic acid is taken out from an upper portion of the multistage tower, while an aqueous slurry of terephthalic acid is taken out from a lower portion. This substitution method relies on the sedimentation of terephthalic acid particles in the tower, whereby setting up or scaling up of the operation conditions is not easy. Further, mixing of substantial amounts of water and acetic acid is unavoidable, whereby a cost for separating the mixed solution will be substantial.

Further, a method is also proposed wherein an acetic acid slurry of terephthalic acid is introduced to a filter band or a filter cell and subjected to countercurrent multistage washing with water for substitution into an aqueous slurry (EP 502628A, International Patent Publication No. 93/24440, U.S. Pat. No. 5,200,557, etc.). Such a method has a merit in that the drying step can be omitted, but a large amount of a mixture of water and acetic acid will still form, whereby a cost for separating such a mixture will be substantial.

It is an object of the present invention to provide a simple and efficient improved process which can be substituted for a process which comprises drying and storing crude terephthalic acid and preparing an aqueous slurry, and to establish an economical process whereby the cost for separation can be reduced by suppressing mixing of acetic acid with water in such liquid substitution.

The present inventors have conducted extensive studies in view of the above problems and as a result, have found it possible to solve the problems by adopting a process for solvent substitution which comprises a step of washing terephthalic acid crystallized and separated, with p-xylene or acetic acid ester. The present invention has been accomplished on the basis of this discovery.

Thus, the present invention provides a process for preparing an aqueous slurry of terephthalic acid, which comprises oxidizing p-xylene with molecular oxygen in a liquid phase in an acetic acid solvent in the presence of a catalyst, to obtain an acetic acid slurry of terephthalic acid, separating terephthalic acid crystals from the acetic acid slurry, washing the terephthalic acid crystals containing acetic acid, with p-xylene or an acetic acid ester, and then mixing water thereto.

Now, the present invention will be described in detail.

For the oxidation reaction of p-xylene, a method is employed wherein p-xylene is oxidized in liquid phase with molecular oxygen in an acetic acid solvent in the presence of a catalyst. As the catalyst, a mixture of a transition metal compound and a bromine compound is usually employed. The transition metal compound may, for example, be a bromide, a naphthenate, a carboxylate such as an acetate or an acetyl acetonate of a transition metal such as manganese, cobalt, iron, nickel or chromium. The bromine compound may, for example, be a bromide of e.g. manganese, cobalt, iron, nickel or chromium, hydrobromic acid, sodium bromide, ammonium bromide, dibromoethylene, or tetrabromoethane. The bromide of a transition metal may serve as both the transition metal compound component and the bromine compound component. The molecular oxygen may, for example, be pure oxygen, air, or a mixture of pure oxygen with an inert gas.

Acetic acid as the solvent is used usually in an amount of from 1 to 10 parts by weight per 1 part by weight of the starting material p-xylene, and the acetic acid may contain up to about 30 wt % of water. When a cobalt compound and/or a manganese compound, and a bromine compound, are employed as the catalyst, these compounds are used so that cobalt atoms will be from 10 to 5,000 ppm by weight, manganese atoms will be from 10 to 5,000 ppm by weight, and bromine atoms will be from 10 to 10,000 ppm by weight, relative to the solvent. Whereas, the molecular oxygen to be supplied to the oxidation reactor is usually in such an amount that the oxygen will be from 3 to 20 mols per mol of p-xylene. The reaction is carried out usually at a temperature of from 150° to 230° C. under a pressure of from 2 to 100 atm. The above reaction conditions may optionally be changed, and the oxidation reaction may be stepwisely completed.

From the acetic acid slurry of terephthalic acid thus obtained as a reaction mixture, terephthalic acid is crystallized for separation. The acetic acid slurry of terephthalic acid is usually cooled to a temperature of from 200° to 50° C., preferably from 150° to 80° C. to crystallize terephthalic acid, which is further subjected to solid-liquid separation to recover terephthalic acid in the form of crystals. For the solid-liquid separation, a conventional means such as centrifugal separation or filtration may be employed, and an equipment for separation, such as a centrifugal separator, a centrifugal filter, a pressure filter or a vacuum filter may be employed.

The mother liquor after separation of crystals is composed mainly of acetic acid and a catalyst component and usually contains only slight amounts of other components such as terephthalic acid, an oxidation intermediate and other oxidation by-products. Accordingly, it is usually advisable to recycle from 10 to 90 wt % of the mother liquor to the reaction system. With respect to the remaining portion which is not recycled to the reaction system, acetic acid may be recovered by distillation, and an effective component such as a catalyst may be recovered from the distillation residue.

Further, terephthalic acid crystals may be washed with acetic acid, as the case requires. Such an acetic acid washing solution may be recycled together with the above mother liquor to the reaction system.

Then, in the present invention, the terephthalic acid crystals containing acetic acid, thus separated and recovered from the acetic acid slurry, are washed with p-xylene or an acetic acid ester. The type of the acetic acid ester is not particularly limited so long as it does not adversely affect the oxidation of p-xylene or the reaction for purification by hydrogenation of crude terephthalic acid. However, from the viewpoint of the boiling point or the solubility, an ester which can easily be separated from acetic acid or water, is preferred, and an acetic acid ester having a $C_{1-8}$ or preferably $C_{1-4}$ alkyl group, such as methyl acetate, ethyl acetate or butyl acetate, may, for example, be mentioned.

Washing of the terephthalic acid crystals containing acetic acid is carried out usually by conducting a process which comprises adding p-xylene or an acetic acid ester to the terephthalic acid crystals having acetic acid deposited thereon at a temperature of from room temperature to 130° C. under atmospheric pressure or an elevated pressure for washing, followed by separation, at least once, preferably a plurality of times i.e. from 2 to 4 times. The washing method is not particularly limited, and substitution washing or cake washing by slurrying (slurry washing) is usually conducted. In the substitution washing, p-xylene or an acetic acid ester is sprinkled on a filtration cake of terephthalic acid crystals, or a liquid pool covering the cake is formed, and then p-xylene or an acetic acid ester is permitted to pass therethrough by injection under pressure or by filtration under reduced pressure, to remove acetic acid in the cake. In order to improve the washing efficiency, slurry washing may be carried out as the case requires. In such a case, in the separation apparatus of the cake, p-xylene or an acetic acid ester is added to the cake, followed by stirring to form a slurry, or a stirring vessel for slurrying may separately be provided for washing, and the slurry thus prepared is again separated by filtration. The apparatus for the above washing and separation is not particularly limited. However, a method of employing a pressure filter or a vacuum filter is preferred, and by using equipments such as a pressure Nutsche, a belt filter and a rotary cylindrical filter, a process of filtration, washing, liquid removal and cake removal can be efficiently carried out continuously.

The total amount of p-xylene to be used for washing is usually from 0.1 to 5 times by weight, preferably from 0.2 to 0.7 time by weight, relative to terephthalic acid. When washing is carried out repeatedly, the amount of p-xylene to be used for one washing operation is usually from 0.05 to 3 times by weight, preferably from 0.1 to 0.5 time by weight, relative to terephthalic acid. Likewise, the total amount of an acetic acid ester to be used for washing is usually from 0.1 to 5 times by weight, preferably from 0.2 to 2 times by weight, relative to terephthalic acid. When washing is carried out repeatedly, the amount of an acetic acid ester to be used for one washing operation is usually from 0.05 to 3 times by weight, preferably from 0.1 to 1 time by weight, relative to terephthalic acid. In the case where washing is carried out repeatedly, it is advisable to adopt countercurrent washing not to increase the total amount of p-xylene or an acetic acid ester as a washing liquid.

The liquid obtained by washing with p-xylene contains many useful components such as p-xylene as the starting material for terephthalic acid, an acetic acid component as the solvent for the liquid phase oxidation of p-xylene and some terephthalic acid. Therefore, such a liquid may be recycled to the reaction system. On the other hand, the liquid obtained by washing with an acetic acid ester also contains useful components such as acetic acid as the solvent for the oxidation reaction and some terephthalic acid in addition to the acetic acid ester. Further, the acetic acid ester itself will decompose to form acetic acid in the oxidation reaction system of p-xylene. Therefore the liquid obtained by washing with the acetic acid ester may be recycled to the reaction system. Otherwise, the liquid obtained by washing with the acetic acid ester may be distilled to separate and recover at least a part of the acetic acid ester, and the acetic acid ester may be re-used for washing terephthalic acid crystals containing acetic acid. The residual liquid remaining after separation of at least a part of the acetic acid ester, may be recycled to the reaction system.

Then, with respect to the terephthalic acid crystals washed with p-xylene or an acetic acid ester as described above, the majority of the p-xylene or acetic acid ester used for washing acetic acid, is removed, and then water is mixed thereto to obtain an aqueous slurry of terephthalic acid. The amount of water used for this purpose corresponds roughly to the above-mentioned amount of p-xylene or an acetic acid ester used relative to terephthalic acid. The method for mixing water is not particularly limited, and it may be a method wherein the predetermined amount of water is simply mixed to obtain the aqueous slurry, or a method wherein water is added for substitution washing or slurry washing, and then the predetermined amount of water is added to finally obtain the aqueous slurry.

According to a method for slurry washing by an addition of water to the terephthalic acid crystals having the p-xylene or the acetic acid ester attached thereto, the efficiency for washing the p-xylene or the acetic acid ester is particularly high, whereby the p-xylene or the acetic acid ester can be substantially completely removed by the washing. The washing operation with the aqueous slurry may be conducted only once but may be conducted in a plurality of times e.g. from 2 to four times, in order to increase the efficiency for washing the p-xylene or the acetic acid ester. Further, the washing water may be recovered and re-used.

The aqueous slurry thereby obtained may sometimes contain the p-xylene or the acetic acid ester to some extent. However, separation of such p-xylene or an acetic acid ester is easy. If phase separation takes place when the slurry is left to stand, the upper phase i.e. the p-xylene phase or the acetic acid ester phase may simply be separated. Otherwise, the aqueous washing solution is heated to evaporate and recover the p-xylene or acetic acid ester. The separated p-xylene or acetic acid ester may be re-used as a starting material for the reaction or as the above-mentioned agent for washing the terephthalic acid crystals.

As described above, the majority of the p-xylene or the acetic acid ester deposited on the terephthalic acid crystals is removed to obtain an aqueous slurry of terephthalic acid, which can be supplied by itself to the purification by hydrogenation step. The p-xylene or the acetic acid ester deposited on the terephthalic acid crystals should be recovered as far as possible from the viewpoint of re-using it. However, as will be described hereinafter, there is no particular problem even if the aqueous slurry contains the p-xylene or the acetic acid ester to some extent when the aqueous slurry is subjected to purification by hydrogenation of the terephthalic acid. Here, the p-xylene concentration in the aqueous slurry is usually at most 5%, preferably at most 3%, relative to the terephthalic acid. Likewise, the acetic acid ester concentration in the aqueous slurry is usually at most 10%, preferably at most 5%, relative to the terephthalic acid. If the concentration of the p-xylene or the acetic acid ester is too high, the purification effect will be low such being undesirable.

The aqueous slurry of crude terephthalic acid having thus changed the dispersing medium from acetic acid to water, is subjected to purification by hydrogenation after adjusting the terephthalic acid concentration to a level of usually from 1 to 60 wt %, preferably from 10 to 40 wt %. The aqueous slurry is pressurized and heated to completely dissolve the crude terephthalic acid in water to obtain an aqueous solution, and the aqueous solution is contacted with a platinum group metal usually in the presence of hydrogen at a high temperature under a high pressure for purification by hydrogenation. Namely, the aqueous terephthalic acid solution and the hydrogen gas are supplied to a reactor and contacted with the catalyst usually at a temperature of from 220° to 320° C., preferably from 260° to 300° C. The hydrogen gas may be supplied usually at a rate of from 0.05 to 10 $Nm^3$, preferably from 0.1 to 3 $Nm^3$, per 1,000 kg of the aqueous terephthalic acid solution. As the catalyst containing a platinum group metal, palladium, ruthenium, rhodium, osmium, iridium or platinum, or a metal oxide of such a metal, may, for example, be employed. Such a metal or a metal oxide may be used by itself as the catalyst, or may be used as supported on a carrier such as active carbon, which is insoluble in the aqueous terephthalic acid solution. The hot aqueous solution of terephthalic acid thus treated for purification by hydrogenation, is then cooled usually to a level of from 200° to 70° C. to crystallize terephthalic acid, followed by solid-liquid separation and drying to obtain highly pure terephthalic acid.

Now, the present invention will be described in further detail with reference to Examples. However, it should be understood that the present invention is by no means restricted to such specific Examples.

EXAMPLE 1

A slurry comprising 140 g of 10 wt % water-containing acetic acid and 60 g of crude terephthalic acid obtained by oxidizing p-xylene with molecular oxygen in an acetic acid solvent in the presence of cobalt and manganese compounds and a bromine compound, was subjected to suction filtration at 70° C. by means of a Nutsche funnel having a diameter of 70 mm (using filter paper 5A). Here, the filtration condition was set so that the amount of acetic acid attached to the separated terephthalic acid would be from 8 to 10 wt % relative to the terephthalic acid. Then, p-xylene heated to 70° C. was sprinkled on the terephthalic acid cake layer in the Nutsche funnel in an amount of 0.5 time by weight relative to the terephthalic acid, followed by suction filtration in the same manner as in the case of the above acetic acid, to carry out washing. The contents of acetic acid and p-xylene in the cake after the filtration were analyzed, and the results are shown in Table 1. Then, water heated to 70° C. was sprinkled on the terephthalic acid cake layer in the Nutsche funnel in an amount of 1.2 times by weight relative to the terephthalic acid, followed by suction filtration in the same manner as above. The contents of acetic acid and p-xylene in the cake after the filtration were analyzed, and the results are shown in Table 1.

EXAMPLES 2 to 4

In Example 1, the content of acetic acid in the crude terephthalic acid cake, or the amounts of p-xylene and water were changed, and the results are shown in Table 1. In Example 3, washing with p-xylene was carried out twice.

EXAMPLE 5

To the terephthalic acid cake layer after washing with p-xylene, as described in Example 1, water heated to 70° C. was added to obtain a 30 wt % slurry of terephthalic acid, which was subjected to suction filtration. The contents of acetic acid and p-xylene in the cake after the filtration were analyzed, and the results are shown in Table 1.

EXAMPLE 6

To the terephthalic acid cake layer after washing with p-xylene, as described in Example 1, water heated to 70° C. was added to obtain a 30 wt % slurry of terephthalic acid, and the slurry was left to stand. The contents of acetic acid and p-xylene in the sedimented cake (water content: about 50 wt %) were analyzed, and the results are shown in Table 1.

TABLE 1

| | | Example No. | | | | | |
|---|---|---|---|---|---|---|---|
| | | 1 | 2 | 3 | 4 | 5 | 6 |
| Acetic acid content in the crude terephthalic acid cake (wt %) | | 8–10 | 8–10 | 8–10 | 5 | 5 | 5 |
| Amount of p-xylene (weight ratio to terephthalic acid) | | 0.5 | 0.25 | 0.25 × 2 | 0.5 | 1.0 | 0.5 |
| Cake after washing with p-xylene | Acetic acid content (wt %) | 0.3 | 0.7 | 0.1 | 0.1 | 0.1 | 0.1 |
| | p-Xylene content (wt %) | 7.5 | 6.1 | 8.1 | 4.2 | 7.2 | 6.0 |
| Amount of water (weight ratio to terephthalic acid) | | 1.2 | 0.25 | 0.25 × 2 | 0.5 | 2.3 | 2.3 |
| Cake after substitution with water | Acetic acid content (wt %) | 0.1 | 0.4 | 0.1 | 0.1 | 0.1 | 0.2 |
| | p-Xylene content (wt %) | 3.2 | 5.9 | 3.0 | 1.3 | 0.1 | 2.2 |

EXAMPLE 7

To a crude terephthalic acid cake having an acetic acid content of from 8 to 10 wt %, obtained in the same manner as in Example 1, p-xylene heated to 70° C. was sprinkled in an amount of 0.25 time by weight relative to the terephthalic acid, followed by suction filtration, to carry out washing. The amount of acetic acid in the cake after the filtration was 0.5 wt %, and the content of p-xylene was 4 wt %. Water was added thereto to obtain a 30 wt % slurry. This slurry was heated and evaporated under reduced pressure, and the results of the evaporation are shown in Table 2. From Table 2, it is evident that p-xylene used for washing can readily be separated from the aqueous slurry.

TABLE 2

| Solvent distillation rate (%) | Acetic acid distillation rate (%) | p-Xylene distillation rate (%) |
|---|---|---|
| 13 | 6 | 99.0 |
| 24 | 11 | 99.6 |
| 35 | 17 | 99.8 |

EXAMPLE 8

An influence of p-xylene in the aqueous slurry of terephthalic acid over the purification by hydrogenation of crude terephthalic acid, was investigated. The 4CBA content of the crude terephthalic acid used, was 2,000 ppm. Further, 7.5 g of the crude terephthalic acid sample was dissolved in 50 ml of a 2N potassium hydroxide aqueous solution, and the solution was subjected to centrifugal separation at 1,500 G for 15 minutes, whereupon with respect to the supernatant, the alkaline solution transmittance at 340 nm and 400 nm ($T_{340c}$, $T_{400c}$) was determined by means of a quartz cell having an optical path length of 1 cm, whereby $T_{340c}$ was 45%, and $T_{400c}$ was 88%.

18 g of this crude terephthalic acid, 42 g of water and 2 g of a 0.5% Pd/C catalyst were charged into a titanium pressure container having an internal capacity of 100 ml, and 0.5 MPa of hydrogen gas was introduced, followed by a reaction at 280° C. for 18 minutes. After cooling, obtained crystals were separated and dried to obtain terephthalic acid. With respect to the terephthalic acid, $T_{340c}$, $T_{400c}$ and the 4CBA content were analyzed, and the results are shown in Table 3. Then, to the reaction system, p-xylene was added in a predetermined amount relative to the terephthalic acid, followed by purification by hydrogenation, and the analytical results of terephthalic acid thereby obtained are shown in Table 3.

TABLE 3

| Amount of p-xylene (wt %) | $T_{340c}$ (%) | $T_{400c}$ (%) | 4CBA (ppm) |
|---|---|---|---|
| 0 | 85 | 97 | 70 |
| 2 | 85 | 97 | 70 |
| 4 | 84 | 97 | 90 |
| 8 | 80 | 96 | 180 |

EXAMPLE 9

A slurry comprising 140 g of 10 wt % water-containing acetic acid and 60 g of crude terephthalic acid obtained by oxidizing p-xylene with molecular oxygen in an acetic acid solvent in the presence of cobalt and manganese compounds and a bromine compound, was subjected to suction filtration at room temperature by means of a Nutsche funnel having a diameter of 70 mm (using filter paper 5A). Here, the filtration condition was set so that the amount of acetic acid deposited on the separated terephthalic acid would be from 8 to 10 wt % relative to the terephthalic acid. Then, methyl acetate was sprinkled on the terephthalic acid cake layer in the Nutsche funnel in an amount of 0.65 time by weight relative to the terephthalic acid, followed by suction filtration in the same manner as in the case of the above acetic acid. This washing was repeated twice. The contents of acetic acid and methyl acetate in the cake after the filtration were analyzed, and the results are shown in Table 4. Then, water was sprinkled on the terephthalic acid cake layer in the Nutsche funnel in an amount of 0.65 time by weight relative to the terephthalic acid, followed by suction filtration in the same manner as above. This operation was repeated twice. The contents of acetic acid and the methyl acetate in the cake after filtration were analyzed, and the results are shown in Table 4.

EXAMPLES 10 to 16

The test was conducted in the same manner as in Example 9 except that the type of the acetic acid ester, the content of acetic acid in the crude terephthalic acid cake, or the amounts of the acetic acid ester and water or the number of washing operation, was changed, and the results are shown in Table 4. In Examples 11 and 16, washing was carried in such a manner that a predetermined amount of water was added and mixed to the cake after washing with the acetic acid ester to obtain a slurry, followed by suction filtration.

TABLE 4

| | | Example No. | | | | | | | |
|---|---|---|---|---|---|---|---|---|---|
| | | 9 | 10 | 11 | 12 | 13 | 14 | 15 | 16 |
| Type of the acetic acid ester | | Methyl acetate | Methyl acetate | Methyl acetate | Ethyl acetate | Ethyl acetate | Butyl acetate | Butyl acetate | Butyl acetate |
| Amount of the acetic acid ester (weight ratio to terephthalic acid) | | 0.65 × 2 | 0.2 | 0.4 | 0.6 | 0.4 | 0.6 | 0.4 | 0.4 |
| Cake with washing with p-xylene | Acetic acid content (wt %) | 0.1 | 1.1 | 0.6 | 0.6 | 0.7 | 0.6 | 0.7 | 0.7 |
| | Acetic acid ester content (wt %) | 3.6 | 5.2 | 5.5 | 8.3 | 6.6 | 9.0 | 7.8 | 6.9 |
| Amount of water (weight ratio to terephthalic acid) | | 0.65 × 2 | 0.2 | 3.3 | 0.6 | 0.4 | 0.6 | 0.4 | 3.3 |
| Cake after substitution with water | Acetic acid content (wt %) | 0.1 | 0.7 | 0.1 | 0.1 | 0.1 | 0.1 | 0.2 | 0.1 |
| | Acetic acid ester content (wt %) | 0.04 | 0.6 | 0.1 | 1.0 | 0.9 | 5.5 | 5.5 | 0.3 |

According to the present invention, an acetic acid slurry of terephthalic acid produced by liquid phase oxidation of p-xylene in acetic acid can be substituted with water simply and economically without requiring a cumbersome process of drying and storing terephthalic acid and slurrying with water. Further, inclusion of acetic acid in water by this solvent substitution is very little, and this is a substantial merit from the viewpoint of the production cost of terephthalic acid.

What is claimed is:

1. A process for preparing an aqueous slurry of terephthalic acid, which comprises oxidizing p-xylene with molecular oxygen in a liquid phase in an acetic acid solvent in the presence of a catalyst, to obtain an acetic acid slurry of terephthalic acid, separating terephthalic acid crystals from the acetic acid slurry, washing the terephthalic acid crystals containing acetic acid, with p-xylene or an acetic acid ester, and then mixing water thereto.

2. The process according to claim 1, wherein the terephthalic acid crystals containing acetic acid are washed by substitution washing with p-xylene or an acetic acid ester.

3. The process according to claim 1, wherein the terephthalic acid crystals containing acetic acid are washed by slurry washing with p-xylene or an acetic acid ester.

4. The process according to claim 1, wherein the aqueous slurry of terephthalic acid is obtained by subjecting the terephthalic acid crystals washed with p-xylene or an acetic acid ester, to substitution washing with water and then mixing water thereto.

5. The process according to claim 1, wherein the aqueous slurry of terephthalic acid is obtained by subjecting the terephthalic acid crystals washed with p-xylene or an acetic acid ester, to slurry washing with water and then mixing water thereto.

6. The process according to claim 1, wherein the terephthalic acid crystals containing acetic acid are washed with p-xylene.

7. The process according to claim 6, wherein at least a part of the liquid obtained by washing with p-xylene is recycled to the reaction system.

8. The process according to claim 1, wherein the terephthalic acid crystals containing acetic acid are washed with an acetic acid ester containing a $C_{1-4}$ alkyl group.

9. The process according to claim 1, wherein the terephthalic acid crystals containing acetic acid are washed with methyl acetate.

10. The process according to claim 8, wherein the liquid obtained by washing with the acetic acid ester is distilled to separate and recover the acetic acid ester, and the recovered acetic acid ester is re-used for washing the terephthalic acid crystals containing acetic acid.

11. The process according to claim 9, wherein the liquid obtained by washing with methyl acetate is distilled to separate and recover the methyl acetate, and the recovered methyl acetate is re-used for washing the terephthalic acid crystals containing acetic acid.

12. A process for preparing an aqueous slurry of terephthalic acid, which comprises oxidizing p-xylene with molecular oxygen in a liquid phase in an acetic acid solvent in the presence of a catalyst, to obtain an acetic acid slurry of terephthalic acid, separating terephthalic acid crystals from the acetic acid slurry, washing the terephthalic acid crystals containing acetic acid, with p-xylene or an acetic acid ester, then mixing water thereto to obtain an aqueous slurry, and removing p-xylene or an acetic acid ester remaining in the aqueous slurry by phase separation and/or evaporation by heating.

13. The process according to claim 12, wherein the terephthalic acid crystals containing acetic acid are washed by substitution washing with p-xylene or an acetic acid ester.

14. The process according to claim 12, wherein the terephthalic acid crystals containing acetic acid are washed by slurry washing with p-xylene or an acetic acid ester.

15. The process according to claim 12, wherein the aqueous slurry of terephthalic acid is obtained by subjecting the terephthalic acid crystals washed with p-xylene or an acetic acid ester, to substitution washing with water and then mixing water thereto.

16. The process according to claim 12, wherein the aqueous slurry of terephthalic acid is obtained by subjecting the terephthalic acid crystals washed with p-xylene or an acetic acid ester, to slurry washing with water and then mixing water thereto.

17. The process according to claim 12, wherein the terephthalic acid crystals containing acetic acid are washed with p-xylene.

18. The process according to claim 17, wherein at least a part of the liquid obtained by washing with p-xylene is recycled to the reaction system.

19. The process according to claim 12, wherein the terephthalic acid crystals containing acetic acid are washed with an acetic acid ester containing a $C_{1-4}$ alkyl group.

20. The process according to claim 19, wherein the liquid obtained by washing with the acetic acid ester is distilled to separate and recover the acetic acid ester, and the recovered acetic acid ester is re-used for washing the terephthalic acid crystals containing acetic acid.

21. The process according to claim 12, wherein the terephthalic acid crystals containing acetic acid are washed with methyl acetate.

22. The process according to claim 20, wherein the liquid obtained by washing with methyl acetate is distilled to separate and recover the methyl acetate, and the recovered methyl acetate is re-used for washing the terephthalic acid crystals containing acetic acid.

23. A process for producing highly pure terephthalic acid, which comprises oxidizing p-xylene with molecular oxygen in a liquid phase in an acetic acid solvent in the presence of a catalyst, to obtain an acetic acid slurry of terephthalic acid, separating terephthalic acid crystals from the acetic acid slurry, washing the terephthalic acid crystals containing acetic acid, with p-xylene or an acetic acid ester, then mixing water thereto to obtain an aqueous slurry of terephthalic acid, pressurizing and heating the aqueous slurry of terephthalic acid to dissolve the terephthalic acid to obtain an aqueous solution, and contacting the aqueous solution with a platinum group metal catalyst under a high pressure/high temperature condition for purification by hydrogenation.

24. The process according to claim 23, wherein the terephthalic acid crystals containing acetic acid were washed with p-xylene.

25. The process according to claim 23, wherein the terephthalic acid crystals containing acetic acid were washed with an acetic acid ester having a $C_{1-4}$ alkyl group.

26. The process according to claim 23, wherein the terephthalic acid crystals containing acetic acid are washed with methyl acetate.

* * * * *